United States Patent [19]  
Miesel

[11] 3,962,434  
[45] June 8, 1976

[54] 3-ARYL-TRIAZENE-1-OXIDES FOR TREATING INFLAMMATORY DISEASES
[75] Inventor: John L. Miesel, Indianapolis, Ind.
[73] Assignee: Eli Lilly and Company, Indianapolis, Ind.
[22] Filed: Sept. 6, 1974
[21] Appl. No.: 503,580

[52] U.S. Cl. ................................................ 424/226
[51] Int. Cl.² ....................................... A61K 31/655
[58] Field of Search ................................... 424/226

[56] References Cited  
UNITED STATES PATENTS  
3,741,951   6/1973   Hess et al. ........................ 424/226

OTHER PUBLICATIONS  
Chem. Abst. 8th Coll. Index Temp–Tripep p. 31756S.

Primary Examiner—Stanley J. Friedman  
Attorney, Agent, or Firm—Walter E. Buting; Everet F. Smith

[57] ABSTRACT

3-Aryl-triazene-1-oxides are useful for treating inflammatory diseases.

7 Claims, No Drawings

3-ARYL-TRIAZENE-1-OXIDES FOR TREATING INFLAMMATORY DISEASES

BACKGROUND OF THE INVENTION

The etiology and pathogenesis of rheumatic and arthritic diseases remain obscure. Meanwhile the need continues for safer, better tolerated drugs which will slow the progress and alleviate the symptoms of inflammatory diseases. For example in rheumatoid arthritis any agent which reduces the inflammation is important in lessening or delaying the development of crippling.

Certain 1-phenyl-3-methyl-3-hydroxy-triazenes are described as insecticidal agents in Belgian Pat. No. 744930. Other compounds of this class are taught as immunosuppressive agents in Belgian Pat. No. 791322. Although the 3-(substituted-phenyl)-1-alkyltriazene-1-oxides actually have been described in the above mentioned patents as 1-phenyl-3-hydroxytriazenes, similar compounds have been proved to be predominantly the 1-alkyl-3-(substituted-phenyl)triazene-1-oxide isomers [*Tetrahedron Letters*, No. 30, pp. 2593–2596 (1965)]. By convention, the order of numbering of the substituent positions on the two isomers is reversed.

Certain compounds described in the present invention are covered in the beforementioned patents. Anti-inflammatory activity for compounds of the present invention has been heretofore unobserved.

SUMMARY OF THE INVENTION

This invention provides a method of treating inflammatory diseases by administering a compound of the formula:

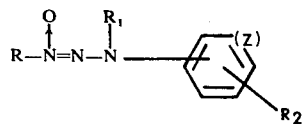

wherein

R is $C_1$–$C_3$ alkyl, $R_1$ is hydrogen or $C_1$–$C_3$ alkyl, $R_2$ is hydrogen, $C_1$–$C_3$ alkyl, $C_1$–$C_3$ alkoxy, or trihalomethyl, and Z is —CH— or nitrogen.

The term "halo" as used herein includes chloro, fluoro, bromo, and iodo. The term "$C_1$–$C_3$ alkyl" includes methyl, ethyl, propyl, and isopropyl.

The term "$C_1$–$C_3$ alkoxy" as used herein refers to methoxy, ethoxy, n-propoxy and isopropoxy.

DETAILED DESCRIPTION

The 3-aryl-triazene-1-oxides employed in this invention are prepared by diazotizing a suitable aniline or aminopyridine with an excess of nitrous acid (generated from sodium nitrite and hydrochloric acid). Excess nitrous acid is destroyed by adding a slight excess of urea. An appropriate $C_1$–$C_3$ N-alkylhydroxylamine hydrochloride is added to a large excess of sodium acetate, and the mixture is added to the diazotized amine. The product is isolated by filtration and recrystallization. The preparation is described in Belgian Pat. Nos. 744930 and 791322 and in *Journ. Ind. Chem. Soc.*, 43, 289–290 (1966).

Illustrative compounds which can be prepared by the above procedure and which are included in the scope of the present invention are:

1-methyl-3-phenyltriazene-1-oxide,
1-ethyl-3-(m-trichloromethylphenyl)triazene-1-oxide,
1-methyl-3-(m-tolyl)triazene-1-oxide,
1-n-propyl-3-(p-anisyl)triazene-1-oxide,
1-methyl-3-(m-anisyl)triazene-1-oxide,
1-methyl-3-(3-pyridyl)triazene-1-oxide,
1-methyl-3-(4-methyl-3-pyridyl)triazene-1-oxide,
1-ethyl-3-(m-trifluoromethylphenyl)triazene-1-oxide,
1-isopropyl-3-(p-tribromomethylphenyl)triazene-1-oxide,
1-methyl-3-(o-ethylphenyl)triazene-1-oxide,
1-n-propyl-3-(p-isopropylphenyl)triazene-1-oxide,
1-ethyl-3-(m-triiodomethylphenyl)triazene-1-oxide,
1-n-propyl-3-[m-(n-propoxy)phenyl]triazene-1-oxide,
1-ethyl-3-(4-n-propyl-2-pyridyltriazene-1-oxide,
1-n-propyl-3-(6-ethoxy-2-pyridyl)triazene-1-oxide,
1-isopropyl-3-(2-trifluoromethyl-4-pyridyl)triazene-1-oxide, and the like.

The 1,3-dialkyltriazene-1-oxides are prepared from the 1-alkyltriazene-1-oxides by generation of the anion at the 3-position of the triazene-1-oxide using a strong base such as sodium hydride and alkylation with an alkyl halide such as methyl iodide and the like.

Illustrative compounds which can be prepared by the above procedure and which are included in the scope of the present invention are:

1,3-dimethyl-3-(p-tolyl)triazene-1-oxide,
1,3-dimethyl-3-phenyltriazene-1-oxide,
1,3-diisopropyl-3-phenyltriazene-1-oxide,
1,3-diethyl-3-(m-trichloromethyl)phenyltriazene-1-oxide,
1-isopropyl-3-methyl-3-(o-ethoxyphenyl)triazene-1-oxide,
1-ethyl-3-isopropyl-3-[p-(n-propyl)phenyl]triazene-1-oxide,
1-ethyl-3-methyl-3-(m-triiodomethylphenyl)triazene-1-oxide,
1-methyl-3-n-propyl-3-(p-isopropoxyphenyl)triazene-1-oxide,
1-n-propyl-3-isopropyl-3-(2-trifluoromethyl-4-pyridyl)triazene-1-oxide,
1-ethyl-3-n-propyl-3-(4-n-propyl-2-pyridyl)triazene-1-oxide,
1-isopropyl-3-ethyl-3-(2-trifluoromethyl-4-pyridyl)-triazene-1-oxide,
1,3-dimethyl-3-(3-pyridyl)triazene-1-oxide,
1,3-diisopropyl-3-(3-pyridyl)triazene-1-oxide, and the like.

The instant invention concerns a method of treating inflammation and its concomitant swelling, fever and ossification in warm-blooded subjects. In particular this invention provides a method of treating inflammatory disorders which comprises orally or parenterally administering daily to a warm-blooded animal suffering from such disorder a compound of the instant invention in a dosage range of from 20 to 100 mg./kg. of animal body weight. At the lower levels of the effective range, one dose of the particular compound is administered, while multiple smaller doses are preferred at the higher levels of the effective range. The preferred dosage range is 20–50 mg., and the preferred method of administration is by the oral route. No deaths of the rats in the carrageenin testing methods were seen when the compounds of the invention were administered at the before-mentioned ranges.

Suitable pharmaceutical formulations adapted for oral administration include powders or granules, soft gelatin capsules, hard gelatin capsules, and tablet formulations.

The anti-inflammatory agents disclosed herein can also be administered as rectal suppositories. Compositions of said rectal suppositories may contain, in addition to the active substances, an excipient such as cacao butter or a suppository wax.

The compounds of this invention also exhibit topical activity and may be applied as creams containing 0.1 to 1 percent by weight of the compound in a vanishing cream or cold cream base or in a water miscible ointment base, for example a polyethylene glycol 4000 base.

Both the erythema blocking assay and the carrageenin paw edema assay were used to demonstrate the activity of the compounds of the invention. In the erythema blocking assay, a modification of the Winder method was used to measure the anti-inflammatory activities of the instant triazene-1-oxides [Winder, C. V,; Wax, J.; Burr, V.; Been, M.; and Posiere, C. E.; A Study of Pharmacological Influences on Ultraviolet Erythema in Guinea Pigs. *Arch. Int. Pharmcodyn.* 116, 261, (1968)]. Albino guinea pigs of either sex, weighing 225–300grams, were shaved on the back and chemically depilated 18–20 hours before exposure to ultraviolet light (Nair, Lotion Hair Remover, Carter Products, N.Y., N.Y.). The animals were fasted overnight. A group of forty-eight animals bearing identifying ear tags were dosed by means of an oral dosing needle. The drugs were administered as suspensions in 1 to 2 cc. of methyl cellulose (Methocell, Dow). The control treatment consisted of administering drug vehicle, Methocell, to a group of four animals. A positive control treatment consisted of giving four animals an effective dose of fenoprofen, 2-(3-phenoxyphenyl)-propionic acid. Ten groups of four animals each were given different dose levels of test compound to obtain dose-responses. Random order and blind administration of the drugs were employed. Forty-eight of the animals were graded and drug identification was made after the animals were graded. The test was considered invalid if the positive control animals did not respond to fenoprofen. Immediately after the guinea pigs were treated, a gummed notebook paper reinforcement was placed on their backs, and they were exposed to a high intensity ultraviolet light for 7 seconds. The ultraviolet light source, a Hanovia Lamp (Kromayer-Model 10), was used to irradiate the skin of the guinea pig's back. After exposure, the reinforcements were removed, and the back was wiped clean with a water-soaked gauze sponge. The unexposed area under the reinforcement provided an area of contrast for grading the erythema. Beginning one hour after exposure and thereafter at half-hour intervals for another 1½ hours, the degree of resulting erythema was graded by an arbitrary scoring system based upon the degree of contrast and redness formed. Anti-inflammatory agents delay the development of the erythema and have their greatest effect at the initial grading periods. The scores were, therefore, weighted by factors of 4, 3, 2, and 1 at the 1.0, 1.5, 2.0, and 2.5 hour scoring times, respectively. The erythema was graded as follows:

| Score | Erythema Scoring System Appearance of Exposed Area |
|---|---|
| 0 | No redness and no contact |
| 1 | Slight redness with a faint reinforcement outline |
| 2 | Slight to moderate redness with a distinct outline |
| 3 | Marked redness with a distinct circular outline |

Total scores from each treatment group of four guinea pigs were compared to the control treatment and the percent inhibition was calculated as follows:

$$100 \times \frac{\text{Control Score} - \text{Treatment Score}}{\text{Control Score}} = \text{Percent Inhibition.}$$

A dose-response graph was obtained by plotting dose versus percent inhibition, the points representing the average of each treatment group of four guinea pigs. The dose ($ED_{50}$) in milligrams per kilogram (mg./kg.) of animal body weight which produced a 50 percent inhibition of the erythemic response for the particular compound tested was obtained by extrapolation. Table I below summarizes the results obtained from testing representative compounds of the invention by the foregoing method. The plotted dose ($ED_{50}$) which represents a 50% inhibition of the erythemic response for the particular compound tested is given in the last column of Table I.

The other test method used in the anti-inflammatory area is the carrageenin testing method. This test shows the ability of compounds to inhibit edema induced by injection of an inflammatory agent into the tissue of a rat as compared with non-treated controls. The procedure is described in detail by C. A. Winter, Proceedings Society of Experimental Biology and Medicine 1962 III, 544. The correlation of the test method with results obtained in humans has been shown by the activities of compounds known to be clinically active including indomethacin, aspirin and butazolidine. Anti-inflammatory edema test results produced by the above method are reported in the first column of Table I.

Table I

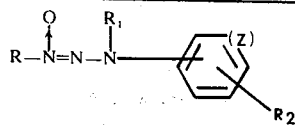

| R | $R_1$ | $R_2$ | Z | Inhibition of Carrageenin Induced inflammatory edema 50 mg/kg | Erythema Blocking 50 mg/kg | Effective Dose (mg/kg) for 50% Inhibition of Erythemic Response |
|---|---|---|---|---|---|---|
| —CH$_3$ | —CH$_3$ | —H | —CH— | 32.9% | 68% | ED$_{50}$ ca. 32 |
| —CH$_3$ | —H | m-OCH$_3$ | —CH— |  | 73% | ED$_{50}$ ca. 23 |
| —CH$_3$ | —H | m-CH$_3$ | —CH— | 30.7% | 85% | ED$_{50}$ ca. 21 |
| —CH$_3$ | H | H | —N— |  | 58% | ED$_{50}$ ca. 41 |
| —CH$_3$ | H | H | —CH— |  | 82% | ED$_{50}$ ca. 27 |
| —CH$_3$ | H | m-CF$_3$ | —CH— |  | 75% | ED$_{50}$ ca. 29 |

The general procedures employed in the preparation of the compounds of this invention are illustrated by the following examples.

EXAMPLE 1

1-Methyl-3-phenyltriazene-1-oxide

To a solution of 9.3 g. of aniline, 25 ml. of 12N hydrochloric acid, and 250 ml. of water was added a solution of 7.0 g. of sodium nitrite in 12 ml. of water in a dropwise manner. After the solution was stirred for 30 minutes at 0°, 2.2 g. of urea was added and the mixture was stirred 15 minutes longer. The chilled solution was added in one portion to a chilled solution of 8.35 g. of N-methylhydroxylamine hydrochloride, 50 g. of sodium acetate and 60 ml. of water. The reaction mixture was stirred at 0°C. for 2 hours and the solid crude product was collected by filtration.

The crude product was dissolved in boiling hexane and filtered while the solution was hot. Cooling the solution and filtering afforded 7.9 g. of product, m.p. 66°–68°C. The N.M.R. spectrum was satisfactory for the 1-methyl-3-phenyltriazene-1-oxide.

Analysis calculated for $C_7H_9N_3O$: (in percent): C, 55.62; H, 6.00; N, 27.80; found (in percent): C, 55.45; H, 5.98; N, 28.08.

EXAMPLE 2

1-Methyl-3(m-trifluoromethylphenyl)triazene-1-oxide

To a solution of 8.05 g. of m-trifluoromethylaniline, 12.5 ml. concentrated hydrochloric acid, and 135 ml. of water agitated at 0°–5°C. was added 3.5 g. of sodium nitrite in 6 ml. of water in small portions. After the mixture was stirred for 30 minutes at 0°C., 1.1 g. of urea was added, and the solution was stirred for 15 minutes. The solution was added in one portion to a mixture of 4.2 g. of N-methylhydroxylamine hydrochloride, 25 g. of sodium acetate, and 40 ml. of water at 5°C. The mixture was allowed to warm to 25°C. and was stirred for 16 hours. The solid crude product was collected by filtration. Recrystallization from hexane afforded 6.9 g. of product, m.p. 87.5°–90°C. The product had a suitable N.M.R. spectrum for the 1-methyl-3(m-trifluoromethylphenyl)triazene-1-oxide.

Analysis calculated for $C_8H_8F_3N_3O$: (in percent): C, 43.84; H, 3.68; N, 19.17; found (in percent): C, 44.04; H, 3.67; N, 19.24.

According to the above procedure m-toluidine was similarly converted to 1-methyl-3-m-tolyltriazene-1-oxide, m.p. 62°–65°C.

EXAMPLE 3

1,3-Dimethyl-3-phenyltriazene-1-oxide

To a solution of 3.0 g. of 1methyl-3-phenyltriazene-1-oxide in 75 ml. of dry dimethylformamide was added 0.9 g. of 57% sodium hydride in mineral oil suspension (10% excess). After the initial evolution of gas had subsided, the reaction mixture was heated at 70° for 30 minutes, then allowed to cool to 25°C. To this reaction mixture was added 3.1 g. of methyl iodide in a quick dropwise manner. After being stirred for 1 hour at 25°C., the mixture was poured into water and extracted with ethyl acetate. The crude extract was evaporated in vacuo and chromatographed on a column of silica gel in benzene. The product was eluted with 20% ethyl acetate in benzene. Recrystallization of the product from hexane yielded 0.9 g. of 1,3-dimethyl-3-phenyl-triazene-1-oxide, m.p. 55°–56°C.

Analysis calculated (in percent): C, 58.17; H, 6.71; N, 25.44; found: C, 57.91; H, 6.93; N, 25.58.

EXAMPLE 4

3-(m-Anisyl)-1-methyltriazene-1-oxide

To a stirred solution of 7.4 g. of m-anisidine in a solution of 15 ml. of 12N hydrochloric acid and 200 ml. of water maintained below 5°C. was added a solution of 4.2 g. of sodium nitrite in 10 ml. of water; the addition of the solution was done in portions. After the reaction mixture was stirred 30 minutes at a temperature below 5°C. to assure formation of the diazonium compound, 1.4 g. of urea was added to destroy the excess of sodium nitrite. The reaction was stirred an additional 10 minutes, then a chilled mixture of 5.0 g. of N-methylhydroxylamine hydrochloride and 30 g. of sodium acetate in 60 ml. of water was added. The reaction mixture was allowed to warm to room temperature and was then stirred 16 hours.

A gummy solid was collected by filtration. Thin layer chromatography indicated a major product plus several impurities. The crude product was dissolved in diethyl ether and chromatographed on 250 ml. of silica gel, using diethyl ether as eluant. Concentration of the product after chromatography, followed by recrystallization from hexane, gave 5.7 g. of 3-(m-anisyl)-1-methyltriazene-1-oxide, m.p. 101°–104°C.

Analysis calculated for $C_8H_{11}N_3O_2$: (in percent): C, 53.03; H, 6.12; N, 23.19 found: C, 53.20; H, 5.93; N, 22.97.

EXAMPLE 5

1-Methyl-3-(3-pyridyl)triazene-1-oxide

To a solution of 9.4 g. of 3-aminopyridine in 31 ml. of 12N hydrochloric acid and 250 ml. of water at 0° was added in small portions a solution of 7.0 g. of sodium nitrite in 12 ml. of water. After the mixture was stirred 30 minutes at 0°, 2.2 g. of urea was added, and the solution was stirred for 15 minutes. The solution was added in one portion to a mixture of 8.35 g. of N-methylhydroxylamine hydrochloride and 50 g. of sodium acetate in 80 ml. of water at about 0° to 5°C. The mixture was stirred over the weekend at 25°C. The reaction mixture was diluted with water and extracted with ethyl acetate three times. The pooled ethyl acetate extract was dried and concentrated to give a mixture of product and recovered 3-aminopyridine. The crude produce was chromatographed on 500 ml. of silica gel using benzene and ethyl acetate mixtures. Solid 1-methyl-3-(3-pyridyl)triazene-1-oxide was obtained by concentration of the mixture of benzene and ethyl acetate from chromatographic elution. Recrystallization of the product from benzene by adding hexane gave 3.3 g. of crystals, m.p. 95°–97°C.

Analysis calculated from $C_6H_8N_4O$: (in percent): C, 47.36; H, 5.30; N, 36.82 Found: C, 47.21; H, 5.02; N, 36.66.

I claim:

1. The method of treating an inflammatory condition which comprises administering to a subject suffering from such condition a compound of the formula

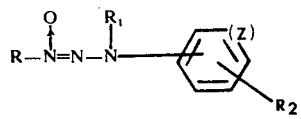

wherein
R is $C_1$–$C_3$ alkyl,
$R_1$ is hydrogen or $C_1$–$C_3$ alkyl,
Z is —CH—, and
$R_2$ is hydrogen, $C_1$–$C_3$ alkyl, $C_1$–$C_3$ alkoxy or trihalomethyl, in an amount sufficient to be effective against the inflammation.

2. The method of claim 1 wherein the compound is administered at a level of 20–100 mg./kg. of body weight per day.

3. The method of claim 2 wherein the compound is 1,3-dimethyl-3-phenyltriazene-1-oxide.

4. The method of claim 2 wherein the compound is 1-methyl-3-(m-tolyl)triazene-1-oxide.

5. The method of claim 2 wherein the compound is 1-methyl-3-(m-anisyl)triazene-1-oxide.

6. The method of claim 2 wherein the compound is 1-methyl-3-phenyltriazene-1-oxide.

7. The method of claim 2 wherein the compound is 1-methyl-3-(m-trifluoromethylphenyl)triazene-1-oxide.

* * * * *